United States Patent [19]

Skakkebæk

[11] Patent Number: 5,250,514
[45] Date of Patent: Oct. 5, 1993

[54] METHOD OF TREATING INFERTILITY OR SUB-FERTILITY IN ADULT MEN, AND THE USE OF PREPARATIONS IN THE METHOD

[75] Inventor: Niels E. Skakkebæk, Farum, Denmark

[73] Assignee: Novo Nordisk A/S, Bagsvaerd, Denmark

[21] Appl. No.: 807,861

[22] PCT Filed: Jul. 27, 1990

[86] PCT No.: PCT/DK90/00194
§ 371 Date: Jan. 13, 1992
§ 102(e) Date: Jan. 13, 1992

[87] PCT Pub. No.: WO91/01747
PCT Pub. Date: Feb. 21, 1991

[30] Foreign Application Priority Data

Jul. 28, 1989 [DK] Denmark .............................. 3725/89

[51] Int. Cl.$^5$ .................... A61K 37/36; A61K 37/38; A61K 37/43
[52] U.S. Cl. .......................................... 514/12; 514/21
[58] Field of Search ....................................... 514/12, 21

[56] References Cited

U.S. PATENT DOCUMENTS

| 4,196,123 | 4/1980 | Rosemberg | 424/177 |
| 4,395,400 | 7/1983 | König et al. | 424/177 |
| 4,751,215 | 6/1988 | Seprodi et al. | 514/15 |
| 4,816,439 | 3/1989 | Jorgensen | 514/12 |
| 5,017,557 | 5/1991 | Fabbri et al. | 514/2 |
| 5,063,204 | 11/1991 | Jacobs | 514/12 |

OTHER PUBLICATIONS

Clin. Endocrinology, vol. 33, pp. 787–807 (1990).

Primary Examiner—Michael G. Wityshyn
Assistant Examiner—Choon P. Koh
Attorney, Agent, or Firm—Steve T. Zelson; Cheryl H. Agris; Sten L. Knudsen

[57] ABSTRACT

Non-surgically correctable infertility or sub-fertility in adult men having poor semen quality is treated with injections of human Growth Hormone (hGH) in daily doses of 1–10 IU/m$^2$ or in doses in combination with gonadotrophins. Increase in total semen volume and total sperm number per ejaculate up to normal figures is obtained.

14 Claims, No Drawings

METHOD OF TREATING INFERTILITY OR SUB-FERTILITY IN ADULT MEN, AND THE USE OF PREPARATIONS IN THE METHOD

The present invention relates to a method of treating non-surgically correctable infertility or sub-fertility in adult men having poor or insufficient semen quality. The invention also relates to the use of human growth hormone (hGH) in the method, either hGH alone or in combination with medical treatment for example gonadotrophins.

There are many causes for infertility or sub-fertility in men, and the medical treatment of this disease is very limited and gives unsatisfactory results.

Depending on the cause of male infertility, the conventional treatment may, for example, comprise either surgery or medical treatment, wherein human chorionic gonadotrophins (hCG), human menopausal gonadotrophin (hMG) (consisting of equal amounts of follicle stimulating hormone, FSH, and luteinizing hormone, LH), luteinizing hormone releasing hormone (LHRH) also called gonadotrophin releasing hormones (GnRH), GnRH analogues or clomiphene citrate may be used.

The invention is based on the discovery that in some cases a connection exists between non-surgically correctable infertility in men and low levels of hGH, and that the poor response obtained in such cases with the above mentioned known treatments might be due to low levels or lack of hGH.

In other cases where low levels or lack of hGH has not been recognized and the above mentioned medical treatments nevertheless have given poor response the present invention has also proven advantageous. Briefly, men with reduced semen quality and with lack of hGH or low to normal level of hGH and where conventional medical treatment has been useless, the treatment with or including hGH according to the invention might be useful.

Adult patients with hGH deficiency (GHD) often complain of fatigue, increased tendency to tiring out, muscle weakness, reduced working capacity and, which is specifically important in this context, of decreased fertility.

It is common practice to subject children having a considerably lower height than normal to a treatment with hGH in order to accelerate growth. When the desired height has been reached no further treatment with hGH is normally carried out due to the scarcity of hGH.

So far, hGH has not been given to adults, even though it is well documented that hGH production and secretion in healthy persons continue in adulthood. One reason for this is that nobody had realized that treatments with hGH would improve semen quality in adults with GHD.

It is known that a connection exists between growth hormone deficiency and poor development of the genitalia of boys. The administration of growth hormone appeared to facilitate growth of genitalia (Laron, Z., and Sarel, R. (1970): Acta Endocrinol. 63: 625–633). Even though hGH improves the growth of genitalia in GHD patients, no investigations have been performed regarding semen quality of such patients.

An object of the invention is to provide a method of treating non-surgically correctable infertility or sub-infertility in adult men having poor or insufficient semen quality and/or demonstrated poor response to known medical treatments.

This object is obtained by the method of the invention, which is characterized in that human growth hormone (hGH) is administered to the male individual to be treated either alone or in combination with medical treatment e.g. gonadotrophins and/or LHRH.

In accordance with a preferred embodiment of the invention, hGH is injected subcutaneously to the male individual to be treated. Other routes of administration can also be used however, such as intramuscular or intravenous injections. In some cases it may be convenient to apply topic preparations, such as lotions or ointments, to penetrate mucous membranes. Also nasal sprays known per se may be used. In fact all forms of administration that will give the necessary uptake of the active compound is useful.

When hGH alone is used the preparation for subcutaneous injections is preferabley used in daily doses containing hGH in amounts of 1–10 IU per $m^2$ body surface, and more preferably 2–6 IU per $m^2$ body surface, and still more preferably 2–5 IU per $m^2$ body surface, divided in several daily doses or given daily or every second day. More than 10 $IU/m^2$ day is considered unnecessary and may cause detrimental side effects. Less than 1 $IU/m^2/day$ may in certain cases be useful when given constantly during several years but will normally be insufficient.

When hGH is given in combination for example with gonadotrophins, these may be used in the form of the naturally occurring human chorionic gonadotrophin (hCG), human menopausal gonadotrophin (hMG), (recovered from urine and containing equal amounts of FSH and LH) and/or the individual components thereof, FSH and LH, separately or in any combination desired. It is also possible to use biosynthetically produced FSH and LH separately or in mixtures.

The doses of hGH will be the same as mentioned above for hGH used alone and the level of gonadotrophins could be as follows:

hMG (1 ampoule containing 75 IU FSH and 75 IU LH)
1–5 ampoules per day, 1–7 times per week combined with hCG 500–10000 IU per day, 1–7 times per week A preferred treatment is
hMG 2 ampoules per day, three times per week and hCG 1500 IU per day, twice per week When hGH is given in conbination with for example LHRH the doses of hGH will still be the same as mentioned above and the dose of LHRH could be given in a pulsatile way with 1–30 μg per pulse every 30–180 min. preferably 2–15 μg per pulse every 60–120 min.

The invention is further illustrated by but not limited to the following examples:

EXAMPLE 1

A 26-year old mand suffering from idiopathic growth hormone deficiency diagnosed at the age of 15 years was treated with human growth hormone for 6 years for improvement of height, but did not receive further treatment during the following 4 years.

The lack of growth hormone production was diagnosed in 1978 by an insulin-hypoglycemic test. A multi-hormone stimulation test was performed with normal results, especially normal thyroid function test and normal response to luteinizing hormone releasing hormone (LHRH) with normal levels of follicle stimulation hormone (FSH) and luteinizing hormone (LH).

The patient started on growth hormone (hGH) in Sep. 1978 with initially 4 IU i.m. twice per week and increasing over the next three years to 2 IU s.c. 6 times per week. This dose was maintained from Nov. 1981 until Aug. 1984 when the hGH treatment was interrupted because the desired final height was achieved. No other treatment was given, except for a supplement of thyroxin for one year in 1981/1982.

No treatment with hGH was given from Aug. 1984 and until Feb. 1987. For improvement of semen analysis, the following treatment was performed:

The patient was initially subjected to placebo injection for 4 months without any improvement of the semen analysis, expecially with regard to volume and total sperm count. After a 4 months "wash-out" period, 2 IU/m$^2$ body surface/day of hGH was injected s.c. for a 4 months period. No significant improvement of sperm quality was observed. However, an improvement of general well-being and an improvement of the secondary sex characteristics like increased growth of beard appeared on hGH treatment.

After a "wash-out" period of 8 months the treatment with hGH was continued in the following way:

2 IU s.c. per day of hGH was initiated and the doses were increased after 3 months to 6 IU s.c. per day. After approximately 4 months treatment with the increased dose of hGH of 6 IU per day, a significant improvement of the semen quality was observed. The results were the following:

Total Sperm Volume

Pretreatment/placebo: 1.6-2.5 ml
On 6 IU hGH per day: 3.5 ml

Total Number of Sperm Per Ejaculate

Pretreatment/placebo: 79-190 millions
On 6 IU hGH per day: 273 millions

EXAMPLE 2

A 40-year-old man with hypogonadotrophic hypogonadism and with infertility problems for 1 year.

Infertility treatment was initiated with LHRH followed by a combination of human menopausal gonadotrophin (hMG) and human chorionic gonadotrophin (hCG) for 12 weeks without any changes in the semen analyses with a sperm count of 0.

A combined treatment of the following was initiated:

| hMG | 2 ampoules | i.m. three times per week |
| hCG | 1500 IU | i.m. twice per week |
| BhGH: | 4 IU | i.m. three times per week |

The result of the semen analyses after 6, 12, 18, and 24 weeks were as follows:

| | Baseline | Week No. of GH treatment | | | |
| --- | --- | --- | --- | --- | --- |
| | | 6 | 12 | 18 | 24 |
| Semen volume | 2 | 3.5 | 4.0 | 2.0 | 2.0 |
| Sperm concentration (sperm/ml) | $0 \times 10^6$ | $0 \times 10^6$ | $2 \times 10^6$ | $6 \times 10^6$ | $26 \times 10^6$ |
| Motility | 0 | 0 | mod. | 60% | 60% |
| Morphology (% abnormal) | 0 | 0 | — | 36% | 28% |

EXAMPLE 3

A 36-year-old man with hypogonadotrophic hypogonadism and being infertile for 7 years.

He had previously had 3 months' therapy of LHRH followed by 3 months of follicle stimulation hormone and luteinizing hormone with no changes in semen analyses and with no sperm in the sperm count.

A treatment consisting of LHRH followed by a combination of hMG/hCG for 12 weeks did not give any improvement of the sperm count either.

A combined treatment of hMG/hCG/B-hGH as mentioned in Example 2 was initiated with the following results after 6 and 12 weeks treatment.

| | Baseline | Week No. of GH treatment | |
| --- | --- | --- | --- |
| | | 6 | 12 |
| Semen volume | 1-2 | 3.5 | 2 |
| Sperm concentration (sperm/ml) | $0-<1 \times 10^6$ | $<1 \times 10^6$ | $6 \times 10^6$ |
| Motility | 0-50% poor progress | — | 40% good progress |
| Morphology (% abnormal) | — | — | 46% |

CONCLUSION

Treatment with growth hormone of a patient with growth hormone deficiency significantly improved the semen quality with increase in total sperm volume and total number of sperm per ejaculate to values closely resembling the values obtained from normal men. The addition of growth hormone to a combined treatment of hMG/hCG to two men with hypogonadotrophic hypogonadism also demonstrated a clear improvement of the semen analyses with significant increase in sperm count from 0 to $26 \times 10^6$ sperm/ml and $0-1 \times 10^6$ sperm/ml to $6 \times 10^6$ sperm/ml. Growth hormone (hGH) is therefore valuable in the treatment of male infertility.

I claim:

1. A method for treating non-surgically correctable infertility or sub-fertility in adult men having poor semen quality comprising administering a preparation of human growth hormone in an amount effective to improve semen quality.

2. A method for treating non-surgically correctable infertility or sub-fertility in adult men having poor semen quality comprising administering preparation of human growth hormone and a preparation of other medical treatment relevant for male infertility or sub-fertility in amounts effective to improve semen quality.

3. The method according to claim 2 in which the preparation of human growth hormone and the preparation of other medical treatment relevant for male infertility or sub-fertility are administered separately.

4. The method according to claim 2 in which the preparation of other medical treatment is gonadotrophins.

5. The method according to claim 2 in which the preparation of other medical treatment is lutenizing hormone releasing hormone.

6. The method according to claim 2 in which the preparation of other medical treatment is gonadotrophins and lutenizing hormone releasing hormone.

7. The method according to claim 1 or 2 in which the preparation is administered via injection.

8. The method according to claim 7 in which the preparation is injected subcutaneously or intramuscularly.

9. The method according to claim 7 in which the preparation is administered in daily doses in amounts of 1-10 IU human growth hormone per m² body surface.

10. The method according to claim 7 in which the preparation is administered in second day doses in amounts of 1-10 IU human growth hormone per m² body surface.

11. The method according to claim 7 in which the preparation is administered in daily doses in amounts of 2-6 IU human growth hormone per m² body surface.

12. The method according to claim 7 in which the preparation is administered in daily doses in amounts of 2-5 IU human growth hormone per m² body surface.

13. The method according to claim 7 in which the preparation is administered in second day doses in amounts of 2-6 IU human growth hormone per m² body surface.

14. The method according to claim 7 in which the preparation is administered in second day doses in amounts of 2-5 IU human growth hormone per m² body surface.

* * * * *